(12) United States Patent
Chhibber et al.

(10) Patent No.: US 6,832,986 B2
(45) Date of Patent: Dec. 21, 2004

(54) ENDOSCOPIC INTUBATION SYSTEM

(75) Inventors: Ashwani Chhibber, Churchville, NY (US); George Berci, Los Angeles, CA (US)

(73) Assignee: Karl Storz GmbH & Co. KG (DE)

( * ) Notice: Subject to any disclaimer, the term of this patent is extended or adjusted under 35 U.S.C. 154(b) by 0 days.

(21) Appl. No.: 09/902,081

(22) Filed: Jul. 10, 2001

(65) Prior Publication Data

US 2002/0137984 A1 Sep. 26, 2002

(30) Foreign Application Priority Data

Mar. 22, 2001 (DE) ..................................... 201 05 206 U

(51) Int. Cl.[7] .................................................. A61B 1/00
(52) U.S. Cl. ...................................... 600/120; 600/138
(58) Field of Search ................................ 600/101, 138, 600/128, 120; 128/200.26

(56) References Cited

U.S. PATENT DOCUMENTS

| | | | | |
|---|---|---|---|---|
| 3,996,939 A | * | 12/1976 | Sheridan et al. | 128/207.14 |
| 4,742,819 A | * | 5/1988 | George | 348/73 |
| 5,329,940 A | * | 7/1994 | Adair | 128/200.26 |
| 5,921,917 A | * | 7/1999 | Barthel et al. | 128/200.26 |
| 5,941,816 A | * | 8/1999 | Barthel et al. | 600/120 |

FOREIGN PATENT DOCUMENTS

| | | | |
|---|---|---|---|
| DE | 20003797 U1 | 6/2000 | |
| JP | 55-81317 | * 6/1980 | 600/120 |
| WO | WO 98/46117 | 4/1998 | |

OTHER PUBLICATIONS

The Role of the Universal Video Intubating System in the Management of the Difficult Airway by Kaplan et al., Published by Endo–Press, Tuttligen, Germany, Sep. 2000.
Endoskope, Volume "Anasthesie," Edition Jan. 1999, pp. AN–DAM–S1 & S2 by STORZ Karl Storz.
Endoskope, Volume "Gynecology," 3rd Edition, Jan. 1999, p. MINI–FET 6 by STORZ Krl Storz.

* cited by examiner

Primary Examiner—Beverly M. Flanagan
(74) Attorney, Agent, or Firm—St. Onge Steward Johnston & Reens, LLC

(57) ABSTRACT

An endoscopic intubation system, in particular for babies or very small childern, comprises an endoscope and an endotracheal tube, where the endoscope includes a substantially bend-resistent shaft whose outer diameter is slightly smaller than an inner diameter of the tube, so that the tube can be slid onto the shaft and where the shaft is at least partially curved. The shaft comprises a continuously curved portion starting from the distal end.

14 Claims, 2 Drawing Sheets

ENDOSCOPIC INTUBATION SYSTEM

BACKGROUND OF THE INVENTION

The invention relates to an endoscopic intubation system, particularly for babies or very small children, with an endoscope and an endotracheal tube, where the endoscope comprises a substantially bend-resistant shaft, whose outer diameter is slightly smaller than an inner diameter of the tube, such that the tube can be slid onto the shaft and where the shaft is at least partially curved.

An intubation system is disclosed in the German product catalogue of Karl Storz GmbH & Co. Kg, Tuttlingen, "STORZ Karl Storz—Endoskope", Volume "Anästhesie", Edition January 1999, page AN-DAM-S1 and 2, which however is not designed for intubation of very small children and especially not for newborn babies.

Such endoscopes are used for intubation of patients, i.e. to introduce an endotracheal tube through the mouth into the trachea under visual control.

Intubation with the aid of an endoscope has the advantage, due to the direct visual control when introducing the tube into the trachea, that the tube can be inserted more precisely and with less trauma to the surrounding tissue. One problem when introducing the tube is to properly distinguish between the esophagus and the trachea. Without visual control when inserting the tube, the treating physician cannot determine whether the tube enters the esophagus or the trachea, which can have fatal consequences if the tube is introduced into the esophagus.

A further danger in intubation is injury of the larynx and in particular to the vocal chords.

On the other hand, the intubation must be carried out very rapidly when respiratory disorders are present or even when breathing has stopped in order to save the life of the patient.

The intubation of newborn babies is particularly problematic, especially for premature babies with respiratory or hemodynamic disorders or very small children with complicated anatomical conditions. Inserting a tube in the trachea is difficult and time-consuming for such very small children due to the very small anatomical structures. The insertion requires a particular aptitude and rapid manipulations.

Currently, the standard procedure for intubation of newborn babies consists of inserting a straight laryngoscope in the mouth of the baby and determining the position of the vocal chords, through which a miniaturized, curved endotracheal tubus having a diameter of 2.5 mm or 3.0 mm is then passed, so to speak in "half-blind" manner. It results from above, that the standard procedure is unsafe due to the deficient visual control when introducing the tube. It is also time-consuming due to the initial introduction of the laryngoscope and the subsequent introduction of the tube.

The above-mentioned known intubation endoscope comprises a bend-resistant or substantially rigid shaft, onto which the tube is slid, which is configured as a flexible tube, on which an adapter for tube fixation is secured. The adapter is configured in the form of a short muff, which is arranged on the rigid shaft to be slidable and can be secured at an arbitrary location on the shaft by a screw.

With such a rigid intubation endoscope, the tube on the rigid shaft is introduced through the mouth into the trachea, whereafter the tube is released from the adapter and the endoscope is withdrawn from the tube.

The shaft of this known endoscope initially runs straight starting from the distal end, then has a relatively short curved region compared to the entire length of the shaft and then continues further in a long straight portion. This known endoscope is not designed for intubation of very small children, especially not newborn or premature babies, due to the form of the shaft.

Flexible intubation endoscopes are also known, for example from the German utility model DE 200 03 797, which also has an adapter for fixing the tube on the flexible shaft of the endoscope. The flexible endoscope is normally not intubated through the mouth but through the nose of the patient. The flexible shaft of such an endoscope can be deflected in different directions with a control unit on the headpiece of the endoscope. However, the use of such an endoscope requires corresponding experience of the physician in handling a flexible endoscope.

A miniature endoscope with a straight bend-resistant shaft having a diameter of only 2 mm, which is used for fetoscopy is also known from the German catalogue of Karl Storz GmbH & Co KG, Tuttlingen, "STORZ Karl Storz-Endoskope", Volume "Gynecology", $3^{rd}$ Edition, January 1999, page MINI-FET 6.

The object of the present invention is to improve an endoscopic intubation system of the above-mentioned type such that a safe, rapid intubation of very small children or babies is possible.

SUMMARY OF THE INVENTION

According to the invention, this object is achieved by an endoscopic intubation system, in particular for babies or very small children, comprising an endotracheal tube having an inner diameter, an endoscope comprising a shaft having a proximal and a distal end, said shaft being substantially bend-resistent and having an outer diameter slightly smaller than said inner diameter of said tube, so that said tube can be slid onto said shaft, said shaft being at least partially curved, wherein said shaft comprises a continuously curved portion starting from said distal end.

In contrast to the standard procedure, it is possible to directly intubate newborn babies under endoscopic visual control with the intubation system of the present invention. The tube slid over the shaft of the rigid endoscope, which takes on the optimal curvature for intubation of newborn babies due to the curvature of the shaft, can be introduced into the trachea of a newborn baby through the mouth under direct visual control. When inserting the endoscope with the tube, the larynx and the vocal chords can be recognized and then the trachea with further insertion, so that an inadvertent intubation into the esophagus can be excluded.

According to the invention, the shaft of the endoscope is already continuously curved from the distal end, which has advantages both from the medical and the technical viewpoints. In contrast to the above-mentioned known endoscopes, the curvature of the shaft already begins at the distal end, i.e. the endoscope of the present intubation system is also curved in the region of the distal end. The curvature continues, preferably over a large region of the shaft compared to its entire length, which allows easy and rapid introduction of the endoscope with the tube in newborn babies.

The technical advantage of this configuration is that the fiber bundles arranged in the shaft for the image transmission system and illumination system are less strongly bent due to the larger radius of curvature of the shaft, compared to the above-mentioned known endoscope where the fiber bundles pass through a curvature of smaller radius. Thus, the optical properties of the present system are improved.

In a preferred embodiment, the radius of curvature of the curved portion of the shaft is approximately constant.

This configuration of the endoscope shaft has been found to be particularly advantageous for the intubation of newborn babies.

In a further preferred embodiment, the curved portion of the shaft extends over at least two thirds of the entire length of the shaft.

With this feature, the endoscope shaft of the present system takes on a curved form over nearly its entire length, which has proven to be particularly advantageous for introduction of the tube, which is also curved, into the trachea.

In a further preferred embodiment, a straight portion follows the continuously curved portion, on which an adapter is arranged for fixing the tube to the shaft.

The advantage is that the relative position of the tube and the endoscope remains unchanged when introducing the endoscope, i.e. the tube cannot inadvertently shift relative to the shaft when inserting the entire arrangement. The straight portion is better suited for the attachment of the adapter due to constructive reasons, because it has not to be adapted to a curvature.

The adapter is preferably axially shiftable and lockable on the shaft.

Due to the shiftability of the adapter, various tube lengths can be used with the endoscope, where despite different tube lengths, the distal end of the tube is always positioned at a predetermined location relative to the distal end of the endoscope. For example, it is advantageous when the distal end of the tube slightly projects beyond the distal end of the shaft, so that injury to the patient caused by the harder end of the endoscope is avoided when introducing the arrangement of the tube and the endoscope.

In a further preferred embodiment, the adapter comprises a connector for connecting an air supply hose.

It is important especially for newborn babies that oxygen be supplied already when inserting the tube. The considerable problem of desaturation often occurs with newborn babies which can be avoided with an additional supply of oxygen. The oxygen flow has the additional advantage that the distal end of the endoscope, where the image receiving window and the light exit window are formed, is held clean and dry during the introduction of the intubation system due to the air stream.

In a further preferred embodiment, the outer diameter of the shaft is just enough smaller than the inner diameter of the tube such that an air gap remains between the shaft and the tube.

With this feature, the shaft is optimally adapted to the employed tube and gives the tube its form stability in the optimal curved shape. In addition, the inlet air feed through the adapter can pass through the gap between the shaft and the tube towards the distal end, where it then exits the tube.

In a further preferred embodiment, a video camera is arranged at the proximal end of the shaft through which an enlarged endoscopic image can be obtained.

The feature is of advantage in view of the very small anatomical structures of newborn babies in the region of the throat and trachea, because these small structures can be better resolved with the enlarged endoscopic image. The endoscopic visual control of the intubation is considerably improved.

Preferably, the video camera is connected to the endoscope through a coupling and is removable from same.

The further advantage is that the endoscope can be removed from the video camera after use and thus separately cleaned or sterilized in an autoclave without harm to the substantially more sensitive camera.

In a further preferred embodiment, the outer diameter of the shaft is in the range of about 1.5 mm to 2.5 mm, preferably is about 2 mm.

The endoscope is optimally adapted to the endotracheal tubes used for newborn babies with these dimensions of the shaft, which normally have an inner diameter of about 2.5 mm or 3.0 mm. For a tube with an inner diameter of 2.5 mm, the outer diameter of the shaft is preferably 2.0 mm.

Further advantages can be taken from the following description and the attached drawings. It will be understood that the above-mentioned features and those to be discussed below are applicable not only in the given combinations, but may also be used in other combinations or taken alone without departing from the scope of the present invention.

BRIEF DESCRIPTION OF THE DRAWINGS

An embodiment of the invention is illustrated in the drawings and will be described in more detail below with reference thereto.

DETAILED DESCRIPTION OF A PREFERRED EMBODIMENT

Figure 1:
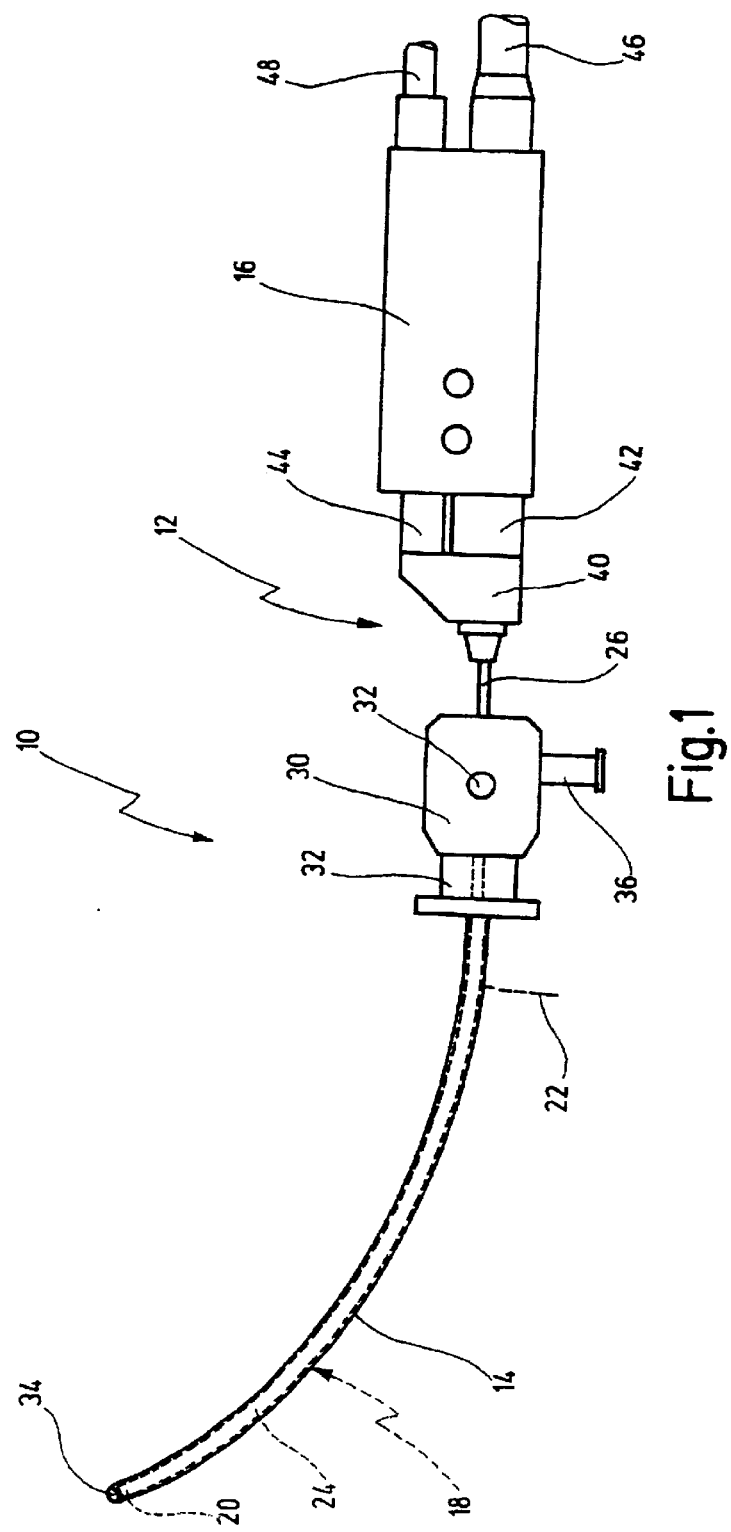
FIG. 1 shows a side view of a total illustration of an endoscopic intubation system with endoscope, tube and video camera in ready condition.
Figure 2:
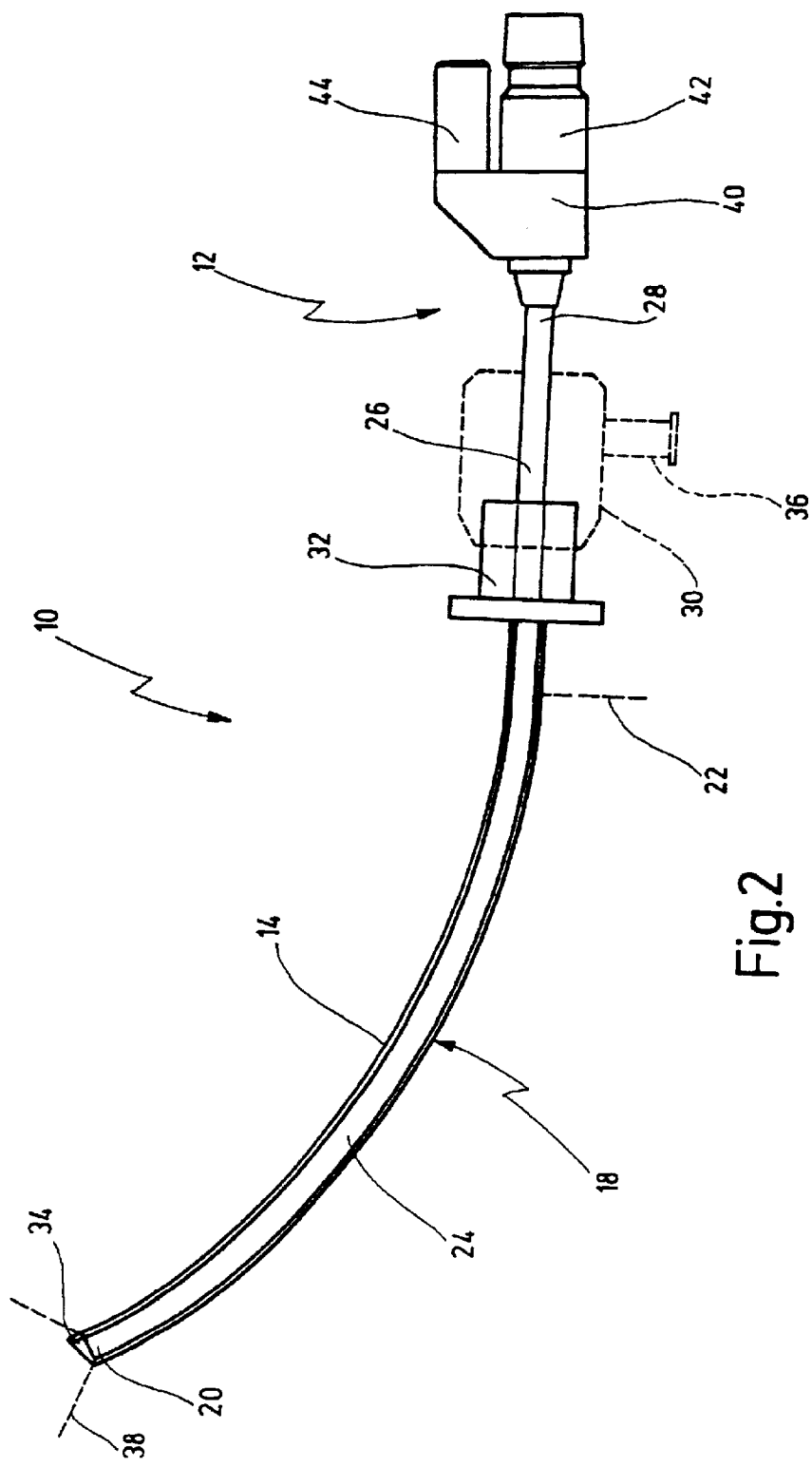
FIG. 2 shows a side view of the endoscope alone of the intubation system of FIG. 1 in an enlarged scale compared to FIG. 1.

An endoscopic intubation system is illustrated in FIGS. 1 and 2 with the numeral 10, which is used for intubating newborn babies.

On the whole, the intubation system 10 comprises an endoscope 12, an endotracheal tube 14 and a video camera 16. However, the endoscope 12 can also comprise a common ocular in a less expensive configuration for viewing through the endoscope 12 instead of the video camera 16.

The endoscope 12 comprises an elongate shaft 18. Shaft 18 has a curvature, where this curvature extends over a portion 24 of the shaft 18, which runs from a distal end 20 of the shaft to a phantom line 22. As can be seen in FIGS. 1 and 2, the radius of curvature is large and is on the order of the length of the shaft 18.

A straight portion 26 of the shaft joins to the curved portion 24, which extends from a phantom line 22 to a proximal end 28 of the shaft.

The radius of curvature of the curved portion 24 is about constant. As can be taken from FIG. 2, the curved portion 24 of the shaft 18 extends at least over two thirds of the entire length of the shaft 18.

The shaft 18 has an outer diameter of about 2 mm.

The shaft 18 is made of medical steel and is bend-resistant, which will be understood in that the shaft 18 is elastic due to its small diameter, however is not permanently deformable when bent by external forces exerted on the shaft 18. The shaft 18 however has a form stability such that when used for its intended purpose, i.e. for intubation, it does not bend. The shaft 18 is however not flexible in the sense of a flexible endoscope, where the shaft has nearly the flexibility of the optical fiber bundle contained therein. The shaft 18 of the present endoscope 12 can also be referred to as being semi-rigid.

The straight portion 26 of the shaft 18 receives an adapter 30 for affixing the tube 14 to the shaft 18.

The adapter 30 is lockable to the shaft 18 with corresponding securement means, in the present embodiment in the form of a screw 32. When the screw 32 is released, the adapter 30 can be slid off the shaft 18 in its axial direction.

The tube 14 consists of a flexible soft transparent material, which is commonly used for such tubes. The tube 14 in the condition of being removed from the shaft 18 of the endoscope 12 also has a pre-formed curvature, which corresponds to the curvature of the curved portion 24 of the shaft 18. However, a tube can be used which is originally straight and takes on the corresponding curvature of the shaft 18 when slid onto the shaft 18.

A plug 32 is provided at the proximal end of the tube 14, through which the tube 14 can be inserted into the distal end of the adapter 30. The plug 32 sits in the adapter in a press-fit so that no further securement need be provided to fix the plug 32 and therefore the tube 14 onto the adapter 30.

The tube 14 is positioned on the shaft 18 of the endoscope 12, such that a distal end 34 of the tube 14 projects slightly beyond the distal end 20 of the shaft 18. Thus when inserting the arrangement including the shaft 18 and the tube 14, the risk of injuring tissue with the distal end 20 of the shaft 18 of the endoscope 12 is minimized. The distal end 34 of the tube is also formed to be inclined.

The adapter 30 also comprises a connector 36 for connecting an air supply hose (not shown in more detail). Preferably oxygen is supplied in tube 14 through the air hose, passing through the connector 36, the adapter 30 and the plug 32.

To allow the supply oxygen to reach the distal end 34 of the tube 14, the outer diameter of the shaft 18 is smaller than the inner diameter of the tube 14, in the present embodiment about 2.5 mm, just enough that an air gap remains between the shaft 18, whose outer diameter is about 2 mm, and the tube 14. The proximally supplied oxygen can then reach the distal end of the tube 34 through this air gap and exit there into the trachea and lungs when intubating a newborn baby.

A first ordered fiber bundle for the image transmission system and a second unordered fiber bundle for the illumination system (not illustrated in more detail) are arranged in the shaft 18 of the endoscope 12, where the two fiber bundles extend between the distal end 20 and the proximal end 28 of the shaft 18. A lens with a view field angle of about 60° is arranged at the distal end of the shaft 20, so that the anatomical region of the throat is well observed when introducing the endoscope 12. The view field is indicated with broken lines 38. With this indication of the view field 38, it can be taken that the distal end 34 of the tube 14, or at least a partial circumferential section thereof, which extends beyond the end 20 of the endoscope lies in the view field. The tube 14 is advantageously positioned on the shaft 18, which is always possible due to the axial shiftability of the adapter 30 on the shaft 18.

The endoscope 12 comprises a coupling 40 at the proximal end 28 of the shaft 18 for connecting the endoscope 12 to a video camera 16. The first fiber bundle of the image transmission system and the second fiber bundle of the illumination system are separated from one another in the coupling 40, as described for example in WO 98/46117. The first fiber bundle of the image transmission system passes into a first bush 42 and the second fiber bundle of the illumination system into a second bush 44.

The endoscope 12 is releasably connected to the video camera 16 through the coupling 40, which has corresponding receptors for the bushes 42, 44.

A cable 46 is connected to the proximal end of the video camera 16, which supplies electrical signals generated by the image sensor (for example a CCD chip) of the video camera to an image-processing unit, for example a video monitor.

In addition, a further cable 48 is connected to the proximal end of the video camera 16, which supplies light generated by a light source (not shown), for example xenon light, to the second fiber bundle of the illumination system.

The image of the endoscope 12 recorded by the video camera 16 is displayed on a video monitor (not shown) in enlarged representation, so that fine anatomical structures of newborn babies in the region of the mouth, throat and the trachea can be seen in good resolution. In particular, anomalies can be more easily recognized by the enlarged image display.

What is claimed is:

1. Endoscopic intubation system, in particular for babies or very small children, comprising:
   an endotracheal tube having an inner diameter;
   an endoscope, comprising:
      a rigid shaft having a proximal and a distal end, said shaft having a rigid preformed shape with an outer diameter less than 2.5 mm and smaller than said inner diameter of said tube, so that said tube can be slid onto said shaft, the preformed shape of said shaft being at least partially curved having a continuously curved portion extending from said distal end and extending along the length of the shaft to a transition point, and a straight portion extending along the length of the shaft from the transition point to the proximal end.

2. The intubation system of claim 1, wherein a radius of curvature of said curved portion of said shaft is approximately constant.

3. The intubation system of claim 1, wherein said curved portion of said shaft extends over at least two thirds of the entire length of said shaft.

4. The intubation system of claim 1, wherein a straight portion follows said continuously curved portion, upon which an adapter is arranged for fixing said tube on said shaft.

5. The intubation system of claim 4, wherein said adapter is axially shiftable and lockable on said shaft.

6. The intubation system of claim 1, wherein an adapter is arranged on the straight portion of said shaft for fixing said tube on said shaft and wherein said adapter comprises a connector for connecting an air supply hose.

7. The intubation system of claim 1, wherein said outer diameter of said shaft is smaller than said inner diameter of said tube, such that an air gap remains between said shaft and said tube.

8. The intubation system of claim 1, wherein a video camera is arranged at said proximal end of said shaft, through which an enlarged endoscopic image can be obtained.

9. The intubation system of claim 8, wherein said video camera is connected to said endoscope through a coupling and is removable therefrom.

10. The intubation system of claim 1, wherein said outer diameter of said shaft is about 2 mm.

11. An endoscopic intubation system comprising:
   an endotracheal tube;
   an endoscope having a rigid preformed shaft, said shaft having a rigid preformed shape including a curved portion extending from a distal end of the shaft and extending along a length of the shaft to a transition point, and a straight portion extending along a length of the shaft from the transition point to a proximal end of the shaft, the shaft having an outer diameter less than 2.5 mm and insertable into said endotracheal tube; and an adapter located on the straight portion of the shaft for connecting said endotracheal tube to the shaft.

12. The endoscopic intubation system according to claim 11 wherein said adapter is axially moveable on the shaft.

13. The endoscopic intubation system according to claim 11 wherein said adapter is lockable on the shaft.

14. An endoscopic intubation system comprising:

an endotracheal tube having an inner diameter;

an endoscope having a rigid preformed shaft with an outer diameter less than 2.5 mm and smaller than the inner diameter of said tube so that said tube can be slid onto the shaft, the rigid preformed shape of said shaft being at least partially curved having a continuously curved portion extending from a distal end and extending along the length of the shaft to a transition point, and a straight portion extending along the length of the shaft from the transition point to a proximal end.

* * * * *

UNITED STATES PATENT AND TRADEMARK OFFICE
CERTIFICATE OF CORRECTION

PATENT NO. : 6,832,986 B2  Page 1 of 1
APPLICATION NO. : 09/902081
DATED : December 21, 2004
INVENTOR(S) : Ashwani Chhibber et al.

It is certified that error appears in the above-identified patent and that said Letters Patent is hereby corrected as shown below:

Title Page, Item (73) Assignee: should read:

(73)     Assignee: Karl Storz GmbH & Co. KG (DE)
                                University of Rochester
                                Rochester, NY (US)

Signed and Sealed this

Twenty-seventh Day of February, 2007

JON W. DUDAS
*Director of the United States Patent and Trademark Office*